(12) United States Patent
Wood

(10) Patent No.: US 8,097,214 B2
(45) Date of Patent: Jan. 17, 2012

(54) CEILING FAN MOUNTED AIR FRESHENER DEVICE

(76) Inventor: Susan M. Wood, West Palm Beach, FL (US)

( * ) Notice: Subject to any disclaimer, the term of this patent is extended or adjusted under 35 U.S.C. 154(b) by 889 days.

(21) Appl. No.: 11/870,209

(22) Filed: Oct. 10, 2007

(65) Prior Publication Data

US 2009/0098026 A1 Apr. 16, 2009

(51) Int. Cl.
*A62B 7/08* (2006.01)
*A61L 9/00* (2006.01)
(52) U.S. Cl. .......... 422/123; 422/5; 422/120; 422/122
(58) Field of Classification Search .............. 96/296, 96/364; 410/25; 5/730; 422/120, 122, 123, 422/5
See application file for complete search history.

(56) References Cited

U.S. PATENT DOCUMENTS

| | | | |
|---|---|---|---|
| 927,132 A * | 7/1909 | Duenwald | 4/231 |
| 4,197,271 A * | 4/1980 | Fenstermaker et al. | 422/123 |
| 4,258,004 A | 3/1981 | Valenzona et al. | |
| 4,549,693 A * | 10/1985 | Barlics | 239/58 |
| 4,944,898 A | 7/1990 | Glaser | |
| 5,383,765 A | 1/1995 | Baxter et al. | |
| 5,591,504 A * | 1/1997 | Lieberman | 428/68 |
| 5,704,832 A * | 1/1998 | Borrell | 454/157 |
| 5,775,876 A | 7/1998 | Walker et al. | |
| 5,935,526 A * | 8/1999 | Moore | 422/124 |
| 6,254,248 B1 * | 7/2001 | McAuley et al. | 362/101 |
| 6,290,914 B1 * | 9/2001 | LeJeune et al. | 422/125 |
| 6,413,047 B1 | 7/2002 | Green | |
| 6,613,287 B1 | 9/2003 | McElligott | |
| 7,051,400 B1 * | 5/2006 | Saldivar | 15/323 |
| 7,104,755 B2 | 9/2006 | Owens et al. | |
| 7,178,214 B1 * | 2/2007 | Wilson | 29/281.1 |
| 2005/0150973 A1 * | 7/2005 | Brown et al. | 239/6 |
| 2006/0163152 A1 * | 7/2006 | Ward et al. | 210/505 |
| 2008/0305016 A1 * | 12/2008 | Fernandez Torres | 422/123 |

OTHER PUBLICATIONS

U.S. Appl. No. 60/645,680, Bennett, et al. Anisotropic Composite Materials comprising a Plurality of Bonded Fiber Component Structures, Jan. 21, 2005.*

* cited by examiner

*Primary Examiner* — Sean E. Conley
*Assistant Examiner* — Regina M. Yoo
(74) *Attorney, Agent, or Firm* — McHale & Slavin, P.A.

(57) ABSTRACT

The present invention is directed toward an air freshener that is constructed and arranged to be secured to the supporting shaft of a ceiling fan. One embodiment of the device includes a scented ring of wickable material having an inner aperture and split through one side. The aperture is sized to cooperate with the supporting shaft of the fan and the split allows the scented ring to be sprung apart for easy installation of the device about the supporting rod. The wickable material includes properties that allow the device to remain in position about the supporting rod once installed while wicking a fragrance composition substantially to its surface for distributing a fragrance evenly throughout an open area, such as a large room. The inner and bottom surfaces of the scented ring may include a polymeric coating to prevent the fragrance composition from wicking to a supporting surface.

6 Claims, 4 Drawing Sheets

CEILING FAN MOUNTED AIR FRESHENER DEVICE

FIELD OF INVENTION

The present invention generally relates to air fresheners for freshening the air in the surrounding environment, and more specifically to an air freshener device that is mountable on the supporting shaft of a ceiling fan.

BACKGROUND INFORMATION

Various types of air fresheners are commonly used for improving or changing the olfactory characteristics within the interior of a structure such as a home or business.

One common type of air freshener is a two-dimensional, paper fiber card with a fragrance surrounded by a clear plastic envelope. A string or elastic loop is secured to the paper fiber card for suspending the card. The envelope is either pierced or removed and the string or elastic loop is utilized to secure the card in an area to permit the fragrance to be distributed to the room by circulation of the ambient air.

One disadvantage associated with this type of air freshener is that they are typically aesthetically displeasing. Another disadvantage is that the paper fiber card must be suspended in an area where the card does not touch a surrounding surface to prevent the fragrance oils within the card from staining the contacted surface.

U.S. Pat. No. 4,258,004 issued Mar. 24, 1981, to Valenzona et al. discloses a hollow, disc-shaped storage container. The container is attached to a flat surface, via adhesive backed foam, at a suitable location in a room. One or more fragrance discs are placed inside the container, and the top of the container is rotated relative to the bottom to create openings in the side wall of the container. The openings permit the fragrance to be distributed to the room.

One disadvantage associated with this type of air freshener is that they rely on the circulation of the ambient air within the room to distribute the fragrance. Thus, in a large room, these air fresheners are not efficient in distributing the fragrance throughout the entire room.

U.S. Pat. Nos. 4,944,898, 5,383,765, 5,775,876, 6,413,047, 6,613,287, and 7,104,755 disclose air freshener devices constructed to be secured to the blade of a ceiling fan to eliminate the reliance on ambient air for distribution of fragrance.

While these devices are not reliant on ambient air for distribution of fragrance, they have their own set of disadvantages. One such disadvantage associated with this type of device relates to balancing the fan. Because the devices are attached directly to the blade(s) of the fan, counterbalance weight must be utilized for proper operation of the fan. Another disadvantage relates to the possibility of an air freshener detaching from the blade and becoming a projectile.

Accordingly, there exists a need for an air freshener which uniformly distributes a fragrance throughout an entire room. The air freshener should provide a convenient, safe, and disposable means for attaching the air freshener to a support shaft of a ceiling fan. The device should be constructed to prevent spillage or leaching of the fragrance to the supporting fan. The device should be supported out of the reach of children and pets. The device should include a coating, tray, cover or enclosure constructed to various types of liquid and/or solid air freshener.

SUMMARY OF THE INVENTION

Briefly, the present invention is directed toward an air freshener that is constructed and arranged to be secured to the supporting shaft of a ceiling fan. One embodiment of the device includes a scented ring of wickable material having an inner aperture and split through one side. The aperture is sized to cooperate with the supporting shaft of the fan and the split allows the scented ring to be sprung apart for easy installation of the device about the supporting rod. The wickable material includes properties that allow the device to remain in position about the supporting rod once installed, while wicking a fragrance composition substantially to its surface for distributing a fragrance evenly throughout an open area, such as a large room. The inner and bottom surfaces of the scented ring may include a polymeric coating to prevent the fragrance composition from wicking to a supporting surface.

Another embodiment includes a plastic tray constructed and arranged to accept the scented ring of wickable material. Alternatively, the tray may be used to support a ring of cake type air freshener material. The tray includes a lower supporting surface, which may be perforated for air flow. At least one and preferably two walls extend upwardly from the inner and outer perimeter edges of the supporting surface.

Yet another embodiment includes a tubular outer retainer ring having a hinge on one side and a latch on the opposite side thereof which provides mechanical securement between the open ends of the retainer ring. A suitable length of wickable material or scented plastic beads are placed within the aperture extending through the central portion of the retainer ring. Vent apertures in the form of holes or slits extend through the wall of the retainer ring to allow air flow through the retainer ring, whereby operation of the ceiling fan provides uniform distribution of the fragrance throughout an entire area. Damping means may be provided in the form of a removable cover to regulate the dissipation of the scent material through the apertures. In a preferred embodiment, the damping means is a removable cover positioned over some or all of the apertures extending through the side walls of the retainer ring.

Accordingly, it is an objective of the present invention to provide an air freshener for distributing a fragrance evenly throughout an open area, such as a large room.

It is another objective of the present invention to provide an air freshener which can be attached to a ceiling fan supporting rod, so that the operation of the ceiling fan will distribute the fragrance of the air freshener throughout the entire room.

It is yet a further objective of the present invention to provide a storage container for conveniently attaching a fragrance disc or cake to a supporting rod of a ceiling fan.

It is still yet another objective of the present invention to provide a storage container which is reusable so as to permit a fragrance ring constructed and arranged to be attached to the supporting rod of a ceiling fan so as to continuously distribute a fragrance to an entire room at minimal cost.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENTS

Figure 1:
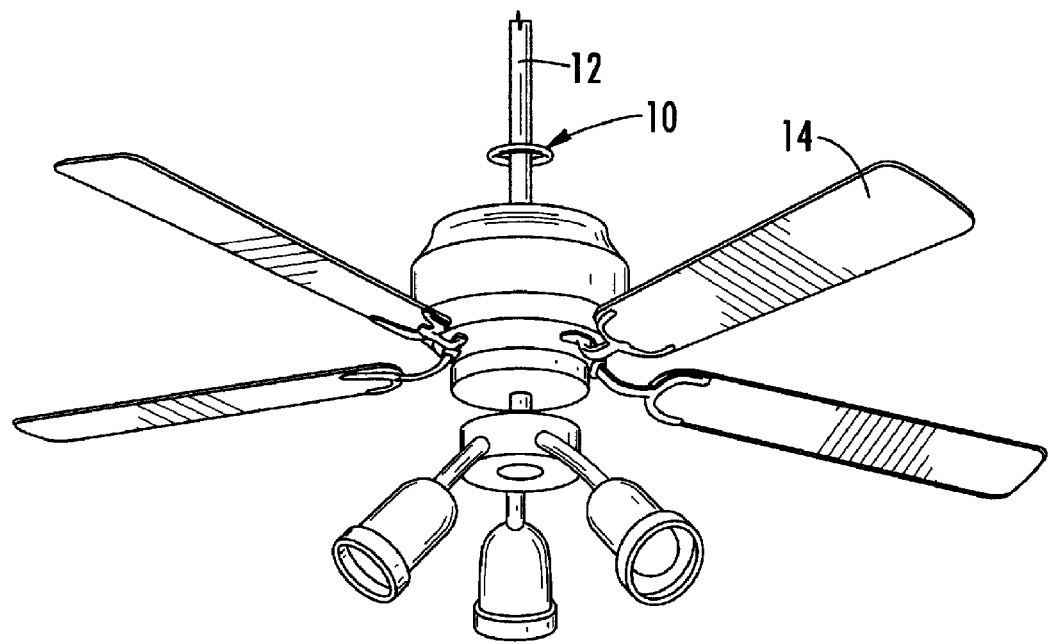
FIG. 1 is a perspective view of one embodiment of the instant invention illustrating the device in cooperation with a supporting rod of a ceiling fan.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiments illustrated.

Referring to FIGS. 1-3 and 8, an air freshener apparatus 10 for attachment about a supporting rod 12 of a ceiling fan 14 is illustrated. One embodiment of the air freshener apparatus includes a scent ring 16 formed of wicking material preferably impregnated with a volatile fragrance material, whereby operation of the ceiling fan provides uniform distribution of fragrance throughout an entire area. In a preferred but non-limiting embodiment, the scent ring is formed from felt material to have an upper surface 18, a lower surface 20, an outer surface 22, and an inner surface 24. The inner surface 24 defines an annular space 28 sized for accepting the supporting rod 12 of the ceiling fan 14 therethrough. A slit 26 extends from the outer surface 22 to the inner surface 24. The scent ring is preferably constructed of a flexible material such as felt so that the ring may be sprung open at the slit to allow the ring to be installed about the supporting rod 12. However, it should be noted that other wicking type materials, as well as polymers, suitable for providing wicking properties may be utilized without departing from the scope of the invention. In one embodiment, illustrated in FIG. 8, at least the inner surface 24 and the lower surface 20 of the scent ring 16 are coated with an impermeable polymeric material such as polypropylene film to prevent the fragrance material from leaching onto the supporting ceiling fan.

Figure 4:
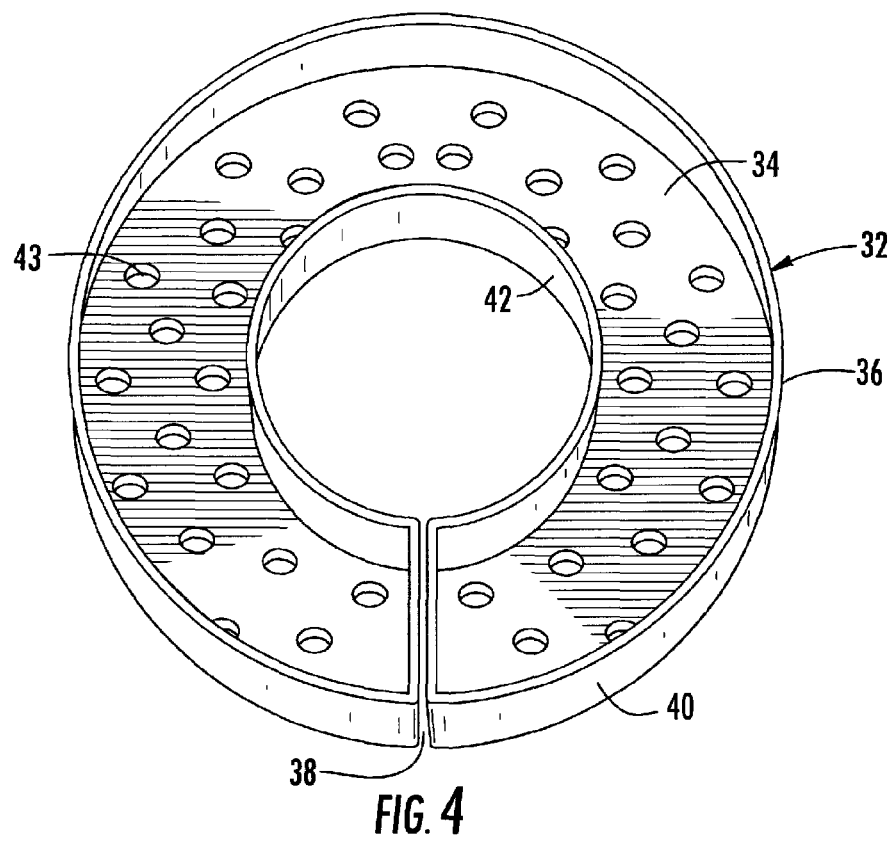
FIG. 4 is a perspective view of a tray constructed to accept the air freshener embodiment illustrated in FIG. 3.
Figure 5A:
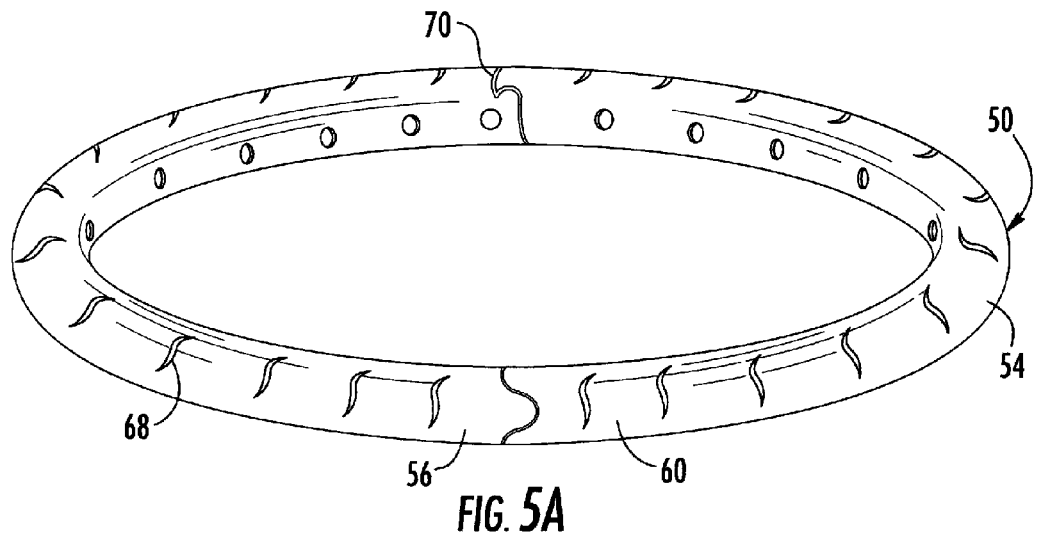
FIG. 5A is a perspective view of one embodiment of the instant invention.
Figure 5B:
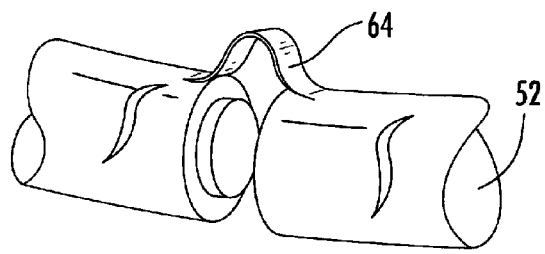
FIG. 5B is a partial perspective view illustrating one embodiment of the instant invention including a living hinge.
Figure 5C:
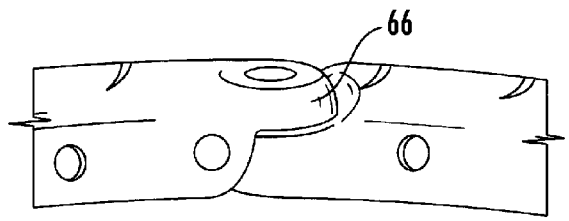
FIG. 5C is a partial perspective view illustrating one embodiment of the instant invention including a pin type hinge.
Figure 5D:
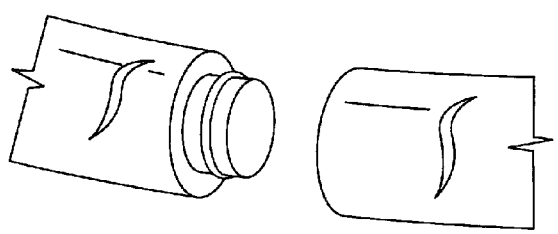
FIG. 5D is a partial perspective view illustrating one embodiment of the instant invention including a friction type latch.
Figure 5E:
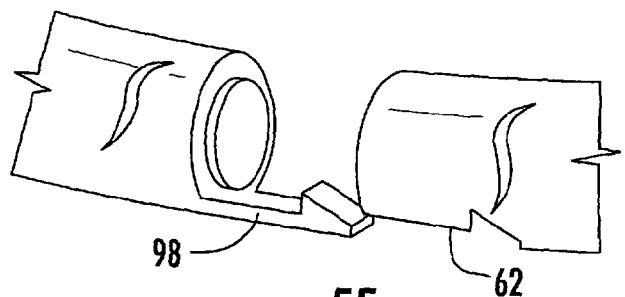
FIG. 5E is a partial perspective view illustrating one embodiment of the instant invention including a catch and receiver type latch.

Referring to FIG. 4, a tray 32 constructed and arranged to contain the scent ring 16 is illustrated. The tray 32 is preferably constructed of an impermeable material, such as plastic, and adapted to hold the scent ring in position about the supporting rod 12. In a preferred embodiment, the tray includes a substantially flat lower surface 34 with a raised rim 36 extending around the perimeter thereof. The tray includes a slit 38 extending from an outer surface 40 thereof to an inner surface 42 thereof whereby the tray is sufficiently flexible for installation about the supporting rod. The tray is generally sized and shaped to accept the scent ring within the confines of the raised rim 36. In one embodiment, the lower surface of the tray includes a plurality of perforations 43 therethrough for increased distribution of the fragrance.

Figure 2:
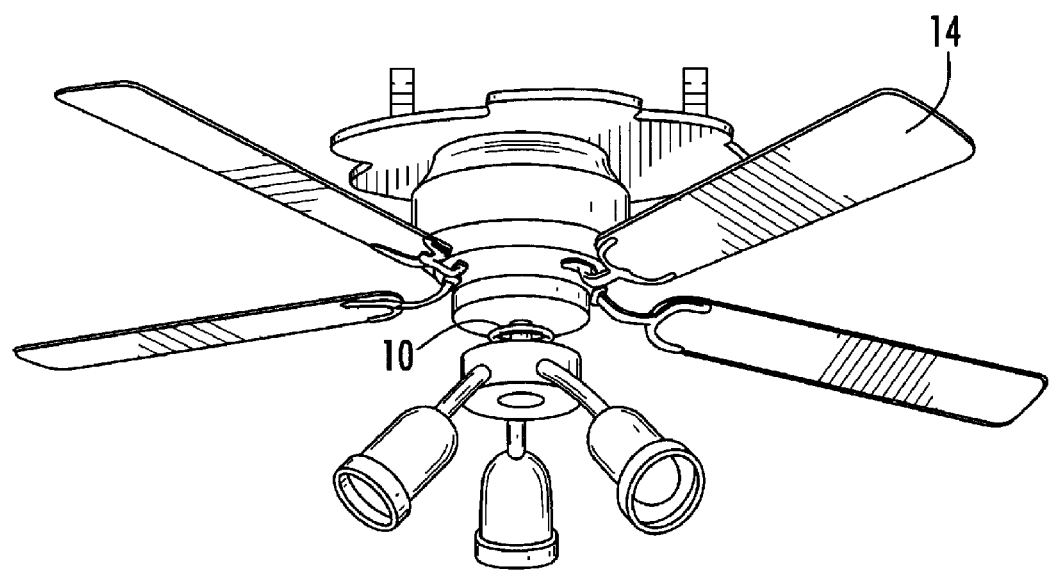
FIG. 2 is a perspective view of one embodiment of the instant invention illustrating the device in cooperation with a supporting rod between a ceiling fan and a light fixture.
Figure 3:
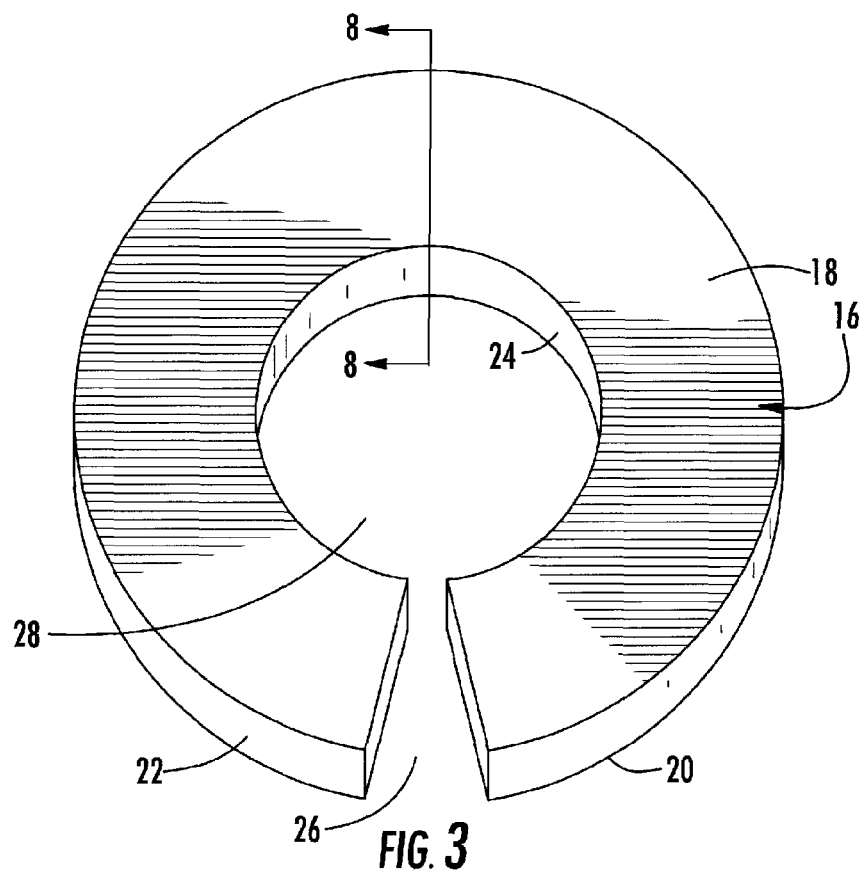
FIG. 3 is a perspective view of one embodiment of the instant invention.

Referring to FIGS. 1-2 and 5, various embodiments of the instant invention including a retainer 50 are illustrated. The retainer 50 is generally constructed of a tubular member 54 defining an annular space 52 sized for accepting a scent ring 16 therethrough. The retainer includes a first end 56 having a latch portion 58 and a second end 60 having a socket portion 62. The second end 60 being constructed and arranged for overlapping interconnection with the first end 56 of the retainer member. It should also be appreciated that the ends of the retainer member may be secured together in a number of ways which may include, but should not be limited to, frictional engagement (FIG. 5D), adhesive (not shown), interfitting components, clamps, tapes and the like. In one embodiment, the retainer is constructed of a sufficiently flexible material to allow the retainer to be flexed open for insertion of the scent ring as well as installation of the air freshener about the support rod of the ceiling fan. In an alternative embodiment, the retainer 50 includes a hinge means constructed and arranged for opening the retainer. In a most preferred embodiment, the hinge means is either a living hinge 64 as illustrated in FIG. 5B or a pin type hinge 66 as illustrated in FIG. 5C. It should also be noted that other hinges well known in the art may be utilized without departing from the scope of the invention.

The retainer 50 may also include a plurality of apertures 68 extending through the wall of the tubular member for dissipation of the fragrance material. All or a portion of the apertures may be covered with a damping means illustrated herein as a removable membrane 70. It should be appreciated that removing all or a portion of the membrane permits a user to regulate the distribution of the fragrance material.

Figure 6:
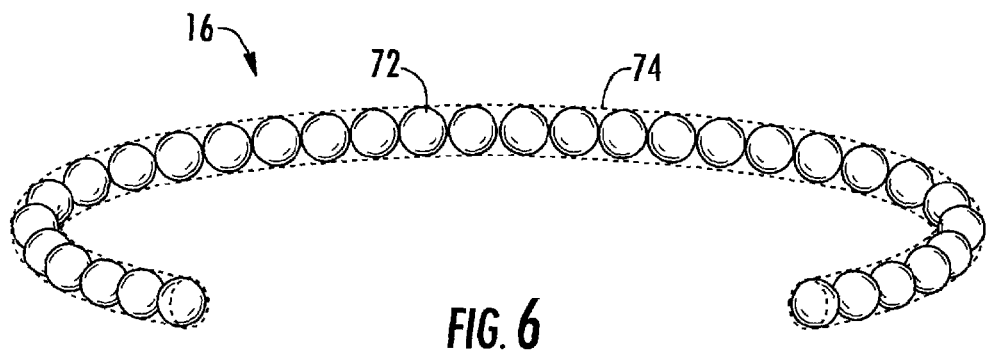
FIG. 6 is a perspective view illustrating a string of scented beads suitable for use with the instant invention.
Figure 7:
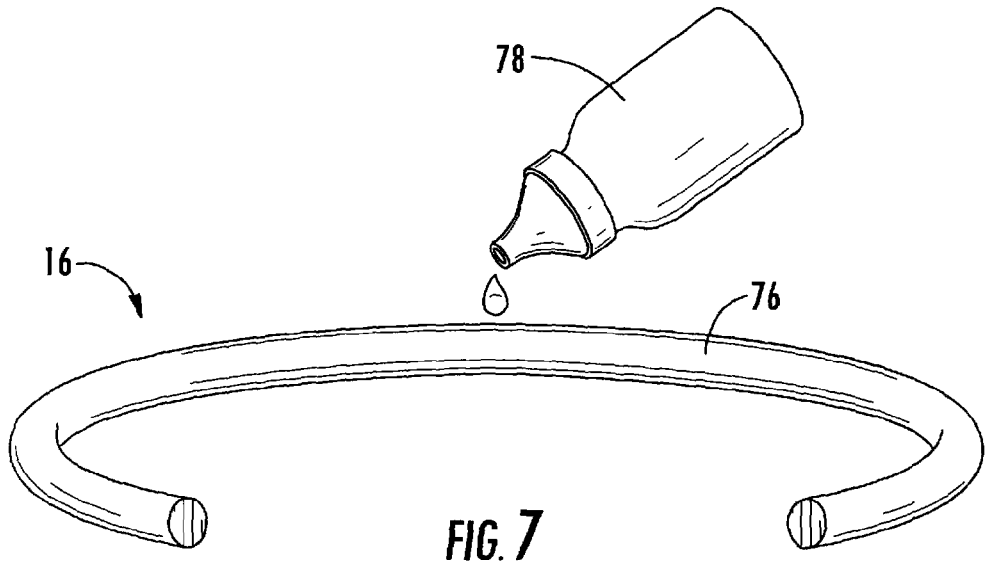
FIG. 7 is a perspective view illustrating a length of wick type material suitable for use with the instant invention.
Figure 8:
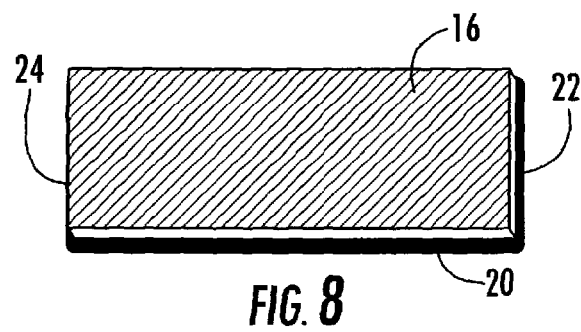
FIG. 8 is a section view taken along lines 8-8 of FIG. 3 illustrating an alternative embodiment of the embodiment shown in FIG. 3 including a polymeric coating on a portion thereof.

Referring to FIGS. 6 and 7, various embodiments of the scent ring 16 are illustrated. FIG. 6 illustrates a scent ring formed from scented beaded plastic 72 within a mesh container 74. Such beads are typically constructed of a polyvinylchloride (PVC) impregnated with fragrance and are available through Dyvex Industries, 30 Enterprise Drive, Carbondale, Pa. The plastic beads are generally sized to fit into the lumen 52 of the retainer and may be replaced when the scent becomes weak or the user desires a new scent. FIG. 7 illustrates a scent ring 16 constructed from a wicking material in the form of a flexible rope 76. The rope is sized to fit within the lumen 52 of the retainer. The rope may be supplied with scent or alternatively may be provided with a container of scent 78 whereby the user can add as much scent as is desired to the wicking material prior to placement within the retainer.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

One skilled in the art will readily appreciate that the present invention is well adapted to carry out the objects and obtain the ends and advantages mentioned, as well as those inherent therein. Any compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An air freshener apparatus for attachment about a supporting rod of a ceiling fan comprising:
 a scent ring formed of wicking material, the scent ring having an upper surface, a lower surface, an outer surface, and an inner surface, a slit extending from said outer surface to said inner surface, said inner surface defining an annular space sized for accepting the supporting rod of the ceiling fan therethrough, said inner surface and said lower surface of said scent ring coated with an impermeable polymeric material, said ring being sufficiently flexible so that said ring may be sprung open at said slit to allow said ring to be installed about said supporting rod, said ring impregnated with a volatile fragrance material, whereby operation of said ceiling fan provides uniform distribution of said fragrance throughout an entire area; and
 a retainer, said retainer constructed of a tubular material formed generally into a circular shape, at least one of the distal ends of the tubular material including a means for securing the distal ends together, the inner lumen of said tubular member being sized for accepting said scent ring.

2. The air freshener apparatus of claim 1 wherein said impermeable polymeric material is a polypropylene film.

3. The air freshener apparatus of claim 1 wherein said retainer includes a hinge means, said hinge means being constructed and arranged for opening said retainer for installation about said supporting rod.

4. The air freshener apparatus of claim 3 wherein said hinge means is a living hinge.

5. The air freshener apparatus of claim 3 wherein said hinge means is a pin type hinge.

6. The air freshener apparatus of claim 1 wherein said retainer is perforated for allowing air flow therethrough.

* * * * *